United States Patent [19]

Johnson et al.

[11] 4,288,608

[45] Sep. 8, 1981

[54] SYNTHESIS OF ANTHRACYCLINES

[75] Inventors: Francis Johnson, Setauket, N.Y.; Kyoung S. Kim, Jeonam, D.P.R. of Korea

[73] Assignee: Research Corporation, New York, N.Y.

[21] Appl. No.: 91,348

[22] Filed: Nov. 5, 1979

Related U.S. Application Data

[62] Division of Ser. No. 911,709, Jun. 1, 1978, Pat. No. 4,196,127.

[51] Int. Cl.$^3$ .............................................. C07C 69/95
[52] U.S. Cl. .................................... 560/53; 562/461
[58] Field of Search .......................... 560/53; 260/351

[56] References Cited

FOREIGN PATENT DOCUMENTS 637093  5/1950  United Kingdom ................ 260/351

Primary Examiner—Paul J. Killos
Attorney, Agent, or Firm—Omri M. Behr

[57]    ABSTRACT

There is provided a novel method of synthesizing certain heterocyclic quinones. In particular there is provided a novel and regiospecific synthesis of 9-acetyl-6,11-dihydroxy-4-methoxy-7,8,9,10-tetrahydronaphthacene-5,12-quinone (7,9-dideoxydaunomycinone) which is known intermediate in the synthesis of daunomycinone. There is also provided a method of preparing analogs of 7,9-dideoxydaunomycinone which thus provide for the preparation of known and desired analogs of daunomycinone. Daunomycinone is a known compound which is an intermediate in the preparation of the clinically accepted naturally-occurring antitumor antibiotics daunomycin and its derivitive adriamycin.

2 Claims, 2 Drawing Figures

SYNTHESIS OF ANTHRACYCLINES

This is a division, of application Ser. No. 911,709, filed June 6, 1978, now U.S. Pat. No. 4,196,127.

BACKGROUND OF THE INVENTION

Adriamycine is an antibiotic compound which is useful in the treatment of certain tumors and is described and claimed in U.S. Pat. No. 3,590,028 to Arcamone, et al. A further procedure for the preparation of adriamycin will be found in U.S. Pat. No. 3,803,124 to Arcamone, et al. Said patent also discloses that adriamycin may be prepared from daunomycin or its aglycone daunomycinone. Another approach may be found in Kende, et al, U.S. Pat. No. 4,070,382.

Most synthetic routes to adriamycin are directed to the synthesis of the tetrahydroxytriketo anthracycline known as daunomycinone. In the synthesis of daunomycinone and its known analogs certain synthetic problems have been noted by workers skilled in the art. Daunomycinone itself carries a methoxy group at the 4-position in the D ring of the anthracycline nucleus. The 4-hydroxy analog, carminomycin is also known, as well as other analogs bearing different substituents at the 1,-2,-3,- and 4-positions of the D ring (see Kende, et al, U.S. Pat. No. 4,021,457.

While several approaches to the synthesis of daunomycinone and its analogs have been disclosed in the art, one of principal difficulties encountered in these syntheses is the provision of regiospecificity in the D ring utilizing regularly available starting materials in a process which is economically feasible on the industrial scale. It will be recognized that where regiospecificity of the substituent (if present) in the D ring is lacking the process utilized would automatically carry a 50% yield penalty to the desired end product regardless of the efficiency of the remaining steps.

The remaining recognized problems of the synthesis of daunomycinone and its analogs lie in possession of the desired substitution pattern at the 7- and 9-positions of the A ring of the anthracycline skeleton. The problems are namely; the provision of an alpha hydroxy group at the 7-position, the provision of an alpha hydroxy group at the 9-position and the provision of a 9-beta acetyl group.

It is of interest in planning molecular modifications of daunomycinone to be able to provide, at the 9-beta position, a substituted carbonyl group other than acetyl for example, propionyl, butyryl, benzoyl, and the like.

The conversion of 7,9-dideoxydaunomycinone to daunomycin is a known procedure set forth in Sih et al., Tet. Lett. 3385 (1976) and Kende, et al, *J. American. Chemical Society* 97, 4425 (1974), the disclosure of which is incorporated herein by reference.

SUMMARY OF THE INVENTION

The present invention provides a mode for the regiospecific synthesis of daunomycinone and its A or D ring substituted analogs with particular reference to the regiospecificity of the substitution pattern in the D ring as well as a mode for variation of the substitution pattern of the carbonyl at the 9-position which is present in daunomycinone as an acetyl moiety. The procedures of the present invention are equally applicable to the synthesis of carminomycinone and its analogs which carry additional substitution in the D ring.

The process of the present invention is exemplified in the general reaction scheme of sequence I set forth in FIG. Ia or Ib. In this sequence the substituent groups $R_1$, $R_2$, $R_3$, and $R_4$ may be the same or different and are each selected from, the group consisting of hydrogen, alkyl, alkoxy, or halo and Q is selected from Br, Cl, I, F, OR or OH. R is alkyl. $R_5$ is alkyl. As will be discussed herein below where one or more of the substituents $R_1$ thru $R_4$ are alkoxy, certain advantages may accrue in selecting the alkyl moiety of $OR_5$ to be different from the alkoxy moieties of $R_1$ thru $R_4$.

The side chain at C-7 is a substituent having para-directing properties on a phenyl nucleus. This substituent may be alkyl or it may be substituted alkyl preferably of 1 to 5 carbon atoms in the skeleton having the partial structural formula, $-CHR_{13}\text{-}(CR_9R_{10})_n\text{-}(CR_{11}R_{12})_m COOR_8$, as shown in FIG. 2, wherein $R_8$ is alkyl, $R_9$, $R_{10}$, $R_{11}$, $R_{12}$ may be the same or different and may be hydrogen, alkyl, $COOR_{15}$ or $COR_{16}$, or may be 0, 1, or 2, provided m+n is at least 2, and $R_{13}$ may be alkyl or hydrogen, $R_{15}$ is lower alkyl of 2-6 carbon atoms and $R_{16}$ is lower alkyl of 1-6 carbon atoms.

As will be seen from FIG. 2 the substitution pattern of the aromatic nucleus of the starting phthalide (I) determines the regiospecificity of the substitution pattern of the D ring of the anthracycline (XI) and similarly the nature of the substituent $R_7$ in the 1,4-dialkoxybenzene starting material (II) determines the nature of the A ring in said anthracycline (XI).

In carrying out the process of the present invention the starting phthalide (I) is reacted with the 1,4-dialkoxybenzene (II) in the presence of a Friedel-Crafts catalyst to yield the Friedel-Crafts condensation product (III) which is then selectively hydrolyzed in aqueous base, suitably in the presence of an alkanol to aid solubilization to yield the corresponding compound (IV) having a terminal carboxylic acid group.

Compound (IV) is then subjected to ring closure and reductive deoxygenation. The ring closure step is carried out by action of Lewis acids, protic acids in the presence of their anhydrides or hydrofluoric acid, the second group being preferred, followed by reduction suitably with an alkyl silane. Isolation of the intermediate ring closed product (Va) is not required. The resulting o-substituted benzoic acid (Vb) is then ring closed in a manner analogous to that utilized to carry out the ring closures in the previous step to yield the anthrone (VI) which may exist either in the keto form as shown, or alternatively in the enol form.

The anthrone (VI) is then oxidized in the usual manner, suitably using a dichromate or chromic acid oxidizing agent to form the corresponding anthraquinone (VII). The anthraquinone (VII) is then sequentially subjected to saponfication and decarboxylation. In one modification of this procedure the saponfication is carried out by a normal base hydrolysis followed by any of the usual procedures for the decarboxylation of a malonic acid, by heating per se or with an acidic or basic decarboxylating agent at a slightly lower temperature. Alternatively, the sequence may be reversed by elimination of one of the alkoxycarbonyl groups with sodium cyanide or the like in a suitable solvent followed by saponfication of the remaining ester group with base in the usual manner. Again, purification of the intermediate product in either case is not required.

The thus produced tetrahydronaphthacenequinone-9-carboxylic acid (IX) is converted into the corresponding 6,11-dialkoxytetrahydronaphthacene quinone (X) having the desired substituted carbonyl at the 9-position. In one modification the acid is first converted into the corresponding acid chloride and then treated with the appropriate organo metallic agent or the acid itself is directly converted to the ketone.

The specific organic moiety attached to the organometallic reducing agent selected will determine the nature of the substituent group on the carbonyl moiety. Thus, where the substituent at C-9 is to be acetyl, as would be the case in the regular daunomycinone series a methyl substituted organometallic alkylating agent would be employed.

The resultant 6,11-dialkoxytetrahydronaphthacene quinone (X) is then subjected to a combination of oxidative dealkylation and reduction reactions to form the corresponding 6,11-dihydroxytetrahydronaphthacenequinone (XI). Certain of the starting materials of general formula (II) are new compounds and are prepared in accordance with the reaction sequence set forth in FIG. II. In the sequence as shown for the formation of daunomycin, $R_9$ and $R_{10}$ are each $COOR_{15}$ and $R_{11}$, $R_{12}$ and $R_{13}$ are hydrogen.

A benzene 1,4-diether (XX) is condensed with a dihalo methylether in the presence of a suitable Friedel-Crafts reagent to yield, upon quenching, the corresponding 2-benzaldehyde 1,4-diether (XXI). This aldehyde is condensed, suitably with the appropriate malonic diester (XXII) and the condensation product, (XXIII) reduced catalytically to yield the corresponding benzyl malonic ester (XXIV) which is further condensed with the appropriate halo alkanoate ester for example methylbromoacetate in the presence of sodium hydride to yield the desired compound (II).

DESCRIPTION OF THE PREFERRED EMBODIMENTS

Figure 1A:
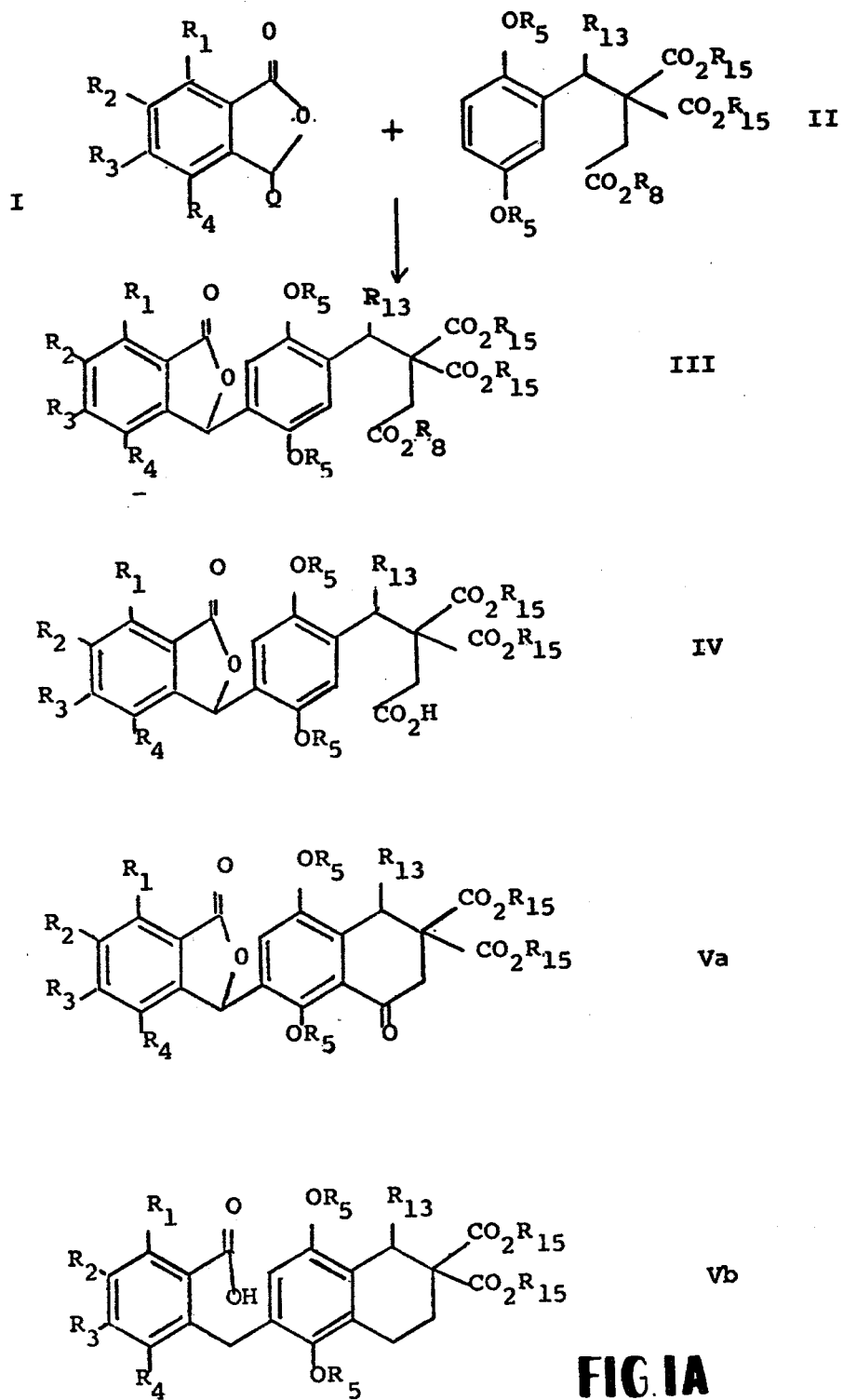
Figure 1B:
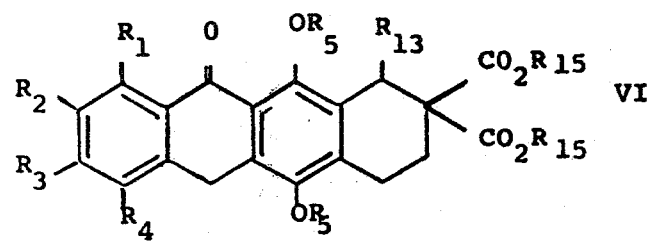
Figure 1B:
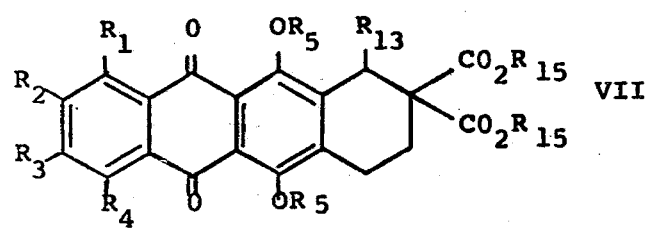
Figure 1B:
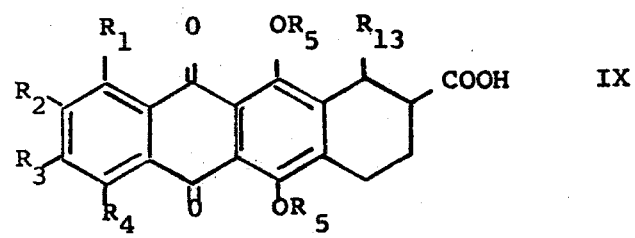
Figure 1B:
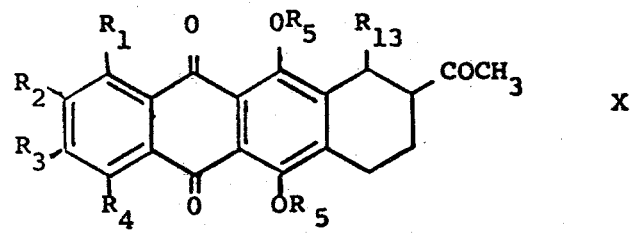
Figure 1B:
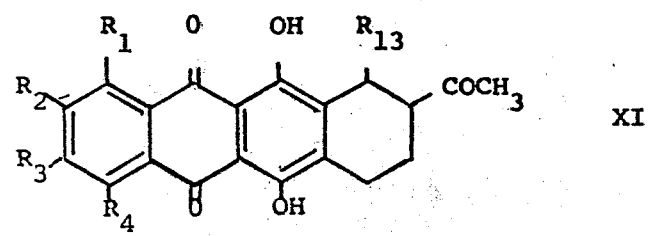
Figure 2:
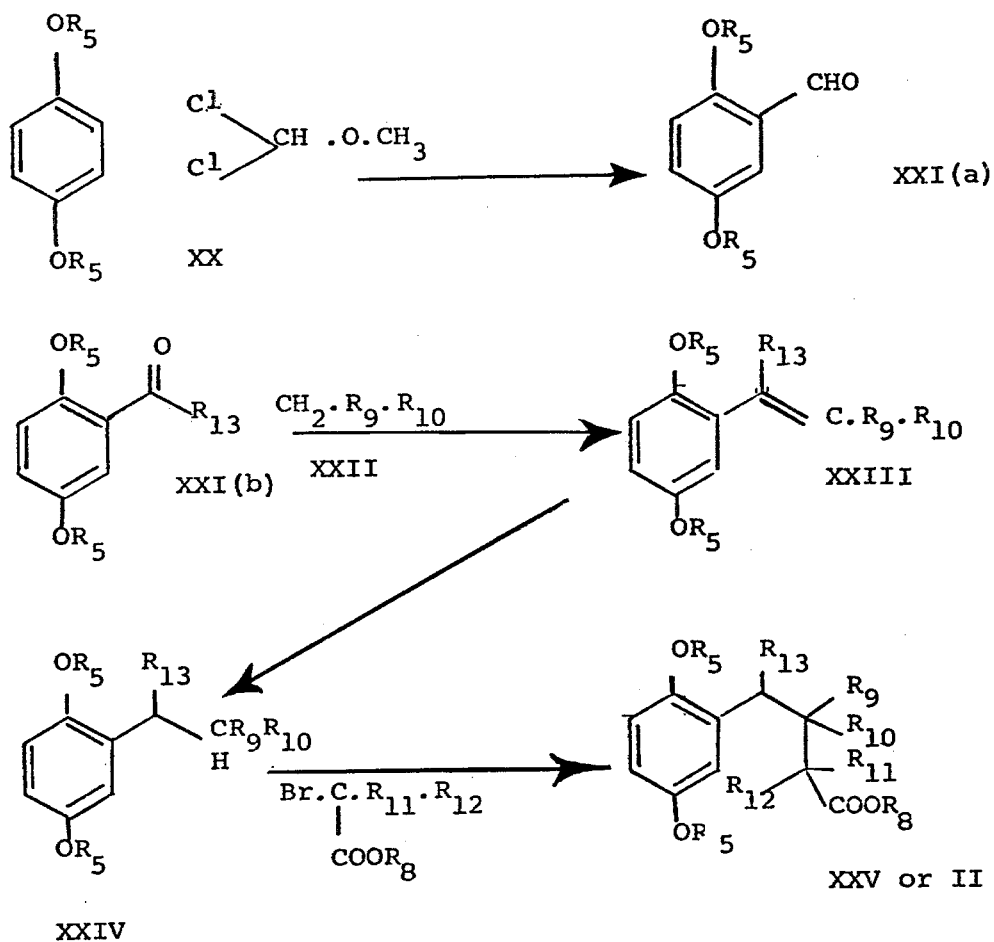

The general procedures for carrying out the process of the present invention are set forth in the flow diagrams of FIGS. Ia, Ib and II.

In these flow diagrams the substituent groups are designated. Thus, $R_1$ thru $R_4$ may be the same or different and are each selected from the group consisting of hydrogen, halo, suitably bromo or chloro, alkyl or alkoxy wherein the alk..moiety comprises 1 to 5 carbon atoms. Most suitably however, the alkyl or alkoxy groups may be methyl or methoxy respectively.

It should be noted that a particular advantage of the present invention resides in the ability to provide an anthracycline carrying any desired substitution pattern in the D ring. Since it is possible to place one or more of the desired and above named substituents at any of positions 4 thru 7 of the phthalide moiety such substituents will be found in the corresponding 1-4 positions of the final anthracycline moiety.

Referring to anthracycline numbering the following substitution patterns are of particular interest. They are listed for purposes of illustration only and not limitation. Unsubstituted, 4-hydroxy (carminomycine), 4-methoxy (daunomycin); 1,4-dimethyl, 1,4-dimethoxy, 2,3-dimethyl, 1,2-dichloro, 2,3-dichloro, 1,3-dichloro, 1,4-dichloro, 1,3- and 2,4-dimethoxy, 1,3- and 2,4-dimethyl, 1-halo-4-methoxy, 4-halo-1-methoxy, 2-halo-4-methoxy, 3-halo-4-methoxy, 3-halo-1-methoxy, 2-halo-1-methoxy, 4-halo-3-methoxy, 4-halo-2-methoxy, in all of the foregoing cases "halo" may be fluoro, chloro, bromo or iodo.

$R_5$ is lower alkyl of 1 to 5 carbon atoms for example methyl, ethyl, propyl, isopropyl, butyl or pentyl. It has been found however that in the final stage of the reaction process, that is to say, the removal of the $R_5$ groups from compound (X) a differential rate of removal exists between the $R_5$ groups and an alkyl component of an alkoxy substituent on the A ring (i.e., where $R_1$ thru $R_4$ may be alkoxy). This differential rate is normally in favor of removal of the $R_5$ groups, which is desirable. It has been found that this differential rate is substantially enhanced in the situation where the alkoxy group on the D ring is methoxy and the group $OR_5$ is ethoxy.

$R_7$ is a substituent having para-directing properties on a phenyl nucleus, it may be a lower alkyl of 1 to 5 carbon atoms or substituted lower alkyl of 1 to 5 carbon atoms in the skeleton. In the synthetic sequence leading to daunomycinone and its analogs it is preferred that the skeleton of $R_7$ comprise 4 carbon atoms in the chain and has the partial structural formula, $CH_2.(CR_9.R_{10})m.(CR_{11},R_{12})n.COOR_8$ wherein $R_8$ is lower alkyl of 1 to 5 carbon atoms, $R_9$ thru $R_{13}$ are the same or different and are selected from the group consisting of hydrogen, lower alkyl of 1 to 5 carbon atoms, $COOR_{15}$ and $COR_{16}$ wherein $R_{15}$ is alkyl of 2-6 carbon atoms, and $R_{16}$ is alkyl of 1-6 carbon atoms, m or n have the value 0, 1 or 2 provided m+n is at least 2. The substituent group Q in compound (I) is halo suitably bromo or chloro most suitably bromo, alkylsulfonyl for example but not limited to mesyl, aralkylsulfonyl most suitably but not limited to tosyl, or alkoxy suitably methoxy.

In the process of the present invention compound (I) is coupled with compound (II) under generally accepted Friedel-Crafts conditions. Any Friedel-Crafts catalyst may be utilized in the reaction. Catalysts such as titanium tetrachloride, zinc chloride, anhydrous aluminum chloride, boron trifluoride and stannic chloride may be utilized; of these, stannic chloride is the most preferred. The reaction is run utilizing substantially stoichiometric proportions. However, it is desirable to use a small excess, say up to 20% by weight of the catalyst. The reaction is carried out in any halocarbon solvent generally utilized for Friedel-Crafts reactions. For example, halogenated hydrocarbons such as chloroform, carbon tetrachloride, dichloroethane, or methylene chloride may be employed; of these, methylene chloride is especially preferred.

The reaction may be carried out at any temperature from about minus 20° C. thru about 80° C. and will be complete in between about 6 to about 2 hours, depending upon the temperature. It has been found convenient however to carry out the reaction at ambient temperature and permit the reaction mixture to stand overnight before work up.

The reaction mixture is quenched suitably by the addition of aqueous acid, for example, 3 N hydrochloric acid. The organic phase is separated, washed with water, dried, suitably over anhydrous magnesium sulfate, and the solvent removed under reduced pressure to yield the compound (III) which may then be recrystallized.

The terminal ester moiety of compound (III) is then selectively saponified by base hydrolysis. This occurs to greatest advantage when $R_{15}=C_2H_5$ and $R_8=CH_3$. Any base of reasonable strength, suitably an alkali metal hydroxide such as sodium or potassium hydroxide is employed. The reaction is carried out in a medium which will solvate both the ester in the base as well as providing an aqueous environment. It has been found suitable to employ a solvent mixture of approximately equal parts of a water soluble ether such as tetrahydrofuran, and alkanols suitably ethanol or methanol. There may be utilized between 1 and 3 equivalents of base per mole of compound (III). However, it has been found suitable to utilize slightly more than 2 equivalents of base per mole of compound (III). The reaction may be carried out at a temperature from about 0° C. to about 100° C. from about 3 to 24 hours. After completion of the reaction, the reaction mixture is acidified with dilute mineral acid and extracted with a water-immiscible reaction inert organic solvent suitably a halogenated hydrocarbon solvent such as methylene chloride, the organic phase is washed, dried and the solvent removed to yield the acid (IV) in substantially quantitative yield.

The acid (IV) is then subjected sequentially to ring closure of the acid moiety to form ring A, and removal of the thus formed keto group by reduction which simultaneously converts the lactone moiety on the potential ring D into an acid moiety. This is followed by a second ring closure between potential ring D and potential ring B to form ring C.

While these steps are set forth herein below (and in the experimental) as discrete steps with actual or partial isolation of the intermediate products such intermediate isolation is not essential as will be indicated at the appropriate point herein below.

The acid (IV) utilized from the preceding step without any further purification, is reacted with a Lewis acid or other suitable acid, if necessary, in a chlorocarbon solvent, or with hydrofluoric acid in a chlorocarbon solvent. Among the Lewis acids which may be employed are boron trifluoride, phosphorus penta-fluoride, or antimony pentafluoride. Protic acids and/or their anhydrides may be used. Suitable reagents in this class are hydrofluoric acid, methane sulfonic anhydride, $P_2O_5$ in methanesulfonic acid and trifluoracetic acid in the presence of trifluoracetic anhydride. The use of the last combination being especially preferred. There is utilized a substantial excess of the Lewis acid, weight for weight equivalent being suitable. The reaction may be carried out at between about 0° C. and 80° C. for from about 0.5 to about 4 hours. As a matter of convenience the reaction may be carried out at ambient temperature and left overnight to insure completion. The reagents are then removed.

In the preferred modification utilizing trifluoracetic acid and trifluoracetic anhydride the solvents may be removed under reduced pressure. Where it is desired to isolate the intermediate A-ring ketone (Va) (not necessary in the full reaction sequence) the residue is made alkaline with a weak mineral base suitably aqueous sodium bicarbonate, extracted with a chlorocarbon solvent and the organic extract washed, dried, and the solvent removed under reduced pressure to yield a residue which may be recrystallized from an alkanol suitably methanol.

The intermediate A ring ketone is then reduced, suitably utilizing any alkyl silane in a suitable acidic medium. Boron trifluoride etherate or acetic acid may be employed. The use of organic acids such as acetic acid however lead to lengthy reaction times. It has been found especially suitable to carry out the reaction in trifluoracetic acid which should of course be substantially anhydrous since the presence of water slows the reaction rate.

Where this reaction is carried out on a large scale there may be added to the reaction mixture of the previous step a sufficient amount of water just sufficient to convert the excess trifluoracetic anhydride to trifluoracetic acid. To this reaction mixture there is added an excess of an alkyl silane, triethylsilane being especially preferred. There is utilized an excess of from about 1.2 to about 4 moles of the silane. The reaction may be carried out under conditions varying from ambient temperature for about 7 days to about 24 hours at about 50° C. The latter, slightly more vigorous conditions being preferred. After completion of the reaction the product may, if desired, be isolated by removal of the solvent under reduced pressure followed by recrystallization, suitably in ether/petroleum ether to give the acid compound (Vb) in a substantially quantitative yield. It is not however necessary to purify compound (Vb).

In the preferred procedure, compound (Vb) is treated with a Lewis acid or a suitable protic acid anhydride under the same conditions as utilized for the first step conversion from compound (III) to the ring A ketone precursor of compound (IV). As stated heretofore, it is preferred to treat the tricyclic acid (Vb) with trifluoracetic acid in the presence of trifluoracetic anhydride at ambient temperature. The reaction in this case is substantially complete in between 0.5 and 1 hours at ambient temperature. The product being the tetrahydronaphthacenol (VI) which, upon analysis, is noted to exist principally in the enolic form rather than in the keto form as shown.

The tetrahydronaphthacenol (VI) is not isolated but oxidized to the corresponding tetrahydronaphthacenequinone (VII). Any oxidizing agent which can convert an anthrone to an anthraquinone may be utilized, however, it is preferred to use sodium dichromate or, most suitably, chromic acid in large excess, an excess of between 1.5 and 3 moles of chromic acid per mole of tetrahydronaphthacenol (VI) being preferred. The reaction may be carried out at between 0° C. to ambient temperature for from about 3 hours to about 15 minutes. It is preferred however to carry out the reaction at about 0° C. for about 30 minutes, thereafter allowing the reaction mixture to warm up to ambient temperature at which temperature the reaction is allowed to complete in about 2 hours. The reaction mixture is then quenched by the addition of water and extracted with a suitable organic water-immiscible solvent suitably ethyl acetate. The organic phase is separated and worked up in the usual manner to yield, after washing, drying and removal of the solvent a residue which may be further purified by filtration thru silica gel to yield a further residue which upon crystallization, suitably from aqueous methanol, yields the tetrahydronaphthacenequinone (VII) in a reasonable yield.

One of the two alkoxycarbonyl groups at the 9-position is then removed with corresponding conversion of the remaining ester group to the corresponding acid. This conversion may be achieved either by saponification followed by decarboxylation or alternatively removal of one of the alkoxy carbonyl groups followed by saponification. The former mode is to be preferred.

In this procedure the tetrahydronaphthacenequinone diester (VII) is saponified by base hydrolysis in the usual manner, heating under reflux with an alkali metal hydroxide suitably sodium or potassium hydroxide in an aqueous alkanol suitably aqueous ethanol for from about 1 to about 4 suitably for about 3 hours is preferred. The reaction mixture is then acidified and extracted with a water-immiscible organic solvent suitably with ethyl acetate. Removal of the solvent under reduced pressure provides the corresponding gem-diacid which may, if desired, be purified by recrystallization, suitably from methylene chloride/ether but such purification is not generally required.

The gem-diacid is then subjected to the usual decarboxylation conditions applicable to a malonic acid. This may be affected either by heating to a range of between 130° C. and 170° C. suitably to about 160° C., or, preferably, the decarboxylation may be carried out in an acidic medium. The gem-diacid may either be heated with aqueous hydrochloric acid in the presence of acetic acid or, most suitably, with acetic acid containing a small amount of piperidine/pyridine—about 5% by volume of each relative to the glacial acetic acid is suitable. The reaction mixture is heated under reflux for from about 30 minutes to about 2 hours suitably for about 1 hour and the solvent removed under reduced pressure to yield the desired monoacid (IX) which may, if desired, be recrystallized in a good yield suitably from ether. The alternative mode is carried out in the following manner.

The diester (VII) is taken up in a polar water-immiscible organic solvent such as dimethyl sulfoxide or dimethyl formamide and heated, suitably under reflux, with an excess, suitably a 1 to 2 molar excess of sodium cyanide for from about 1 to about 4 hours suitably for about 3 hours and the reaction mixture quenched with water. The reaction mixture is extracted with a suitable water-immiscible organic solvent suitably ethyl acetate or the like. The organic layer is separated, washed in the usual manner, dried, and the solvent removed to yield the corresponding anthraquinone-9-monoester which is then saponified in a manner similar to that set forth in the immediately foregoing 2-step procedure to provide, upon work up, the same 9-mono acid (IX).

Compound (IX) is then converted into the desired 9-substituted ketone by treatment with a suitable organometallic alkylating agent. The organic moiety of said alkylating agent will determine the nature of the substituent upon the carbonyl group as will appear immediately herein below.

Two alternate procedures are available. In the first alternate procedure the acid (IX) is converted into the corresponding acid halide in the usual manner. In this procedure the acid (IX) is taken up in a suitable polar water-immiscible organic solvent preferably a halogenated hydrocarbon solvent, most suitably methylene chloride, in the presence of a small amount of basic catalyst such as dimethylformide. Any agent generally utilized for the conversion of carboxylic acids to the corresponding acid halides may be utilized. Among such agents may be mentioned phosgene, triphenylphosphine in carbon tetrachloride, phosphorus oxychloride, phosphorus trichloride, phosphorus pentachloride, phosphorus oxybromide, phosphorus tribromide, and thionyl chloride; the last being especially preferred. There is utilized a substantial excess of the halogenating agent, 2 parts by weight of halogenating agent per part by weight of the acid (IX) being suitable. The reaction is somewhat exothermic and is suitably carried out at ambient temperature and the reaction permitted to go to conclusion, suitably leaving it overnight. The reaction mixture is then worked up suitably by removing the solvent and unreacted halogenating agent (if volatile) under reduced pressure, followed by co-evaporation with benzene to remove the last traces of thionyl chloride where utilized.

The thus produced acid chloride is utilized in the next, alkylation stage without further purification. A very efficient procedure for conversion of an acid chloride to a predetermined corresponding substituted carbonyl involves the reaction of the acid chloride with the corresponding lithium organocuprate. The organo moiety may be alkyl suitably lower alkyl such as methyl, ethyl, butyl, propyl or the like, aryl such as phenyl or napthyl, or aralkyl such as benzyl naphthyl or the like. The foregoing examples are set forth for purposes of exemplification and should in no way be considered to be limiting. The lithium organocuprate is prepared in accordance with the procedure set forth in the *Journal of the American Chemical Society* 94, 5106 (1972). In the preparation of compounds in the daunomycinone series the substituent at the 9-position on the anthracycline nucleus is acetyl, that is to say, the substituent on the carbonyl is methyl. In that case the lithium organocuprate alkylating agent utilized is dimethyl cuprolithium.

The acid chloride of the acid (IX) is taken up in an anhydrous ether, suitably tetrahydrofuran. Some difficulty may be experienced in dissolving the acid chloride in the solvent and heating may be required. The reaction however, must be carried out at low tempeatures from for example about minus 78° C. to about plus 20° C. most suitably at about 30° C. A substantial excess say a 1.2 to 4 molar excess of the lithium organocuprate compound in an etheral solvent, suitably diethyl ether, is prepared and cooled to the reaction temperature which is maintained by external cooling. The warm solution of the acid chloride is then added slowly, with stirring, in an inert atmosphere, to the lithium organocuprate solution. In the preferred mode after about 30 minutes to 2 hours, the cooling agent is removed and the reaction permitted to warm to ambient temperature at which temperature it is maintained for from about 1 to about 5 hours.

The reaction mixture is quenched with a proton donor, suitably saturated aqueous ammonium chloride and the resultant mixture extracted with a water-immiscible reaction inert polar organic solvent suitably with ethyl acetate. The organic extract is washed, dried and the solvent removed to yield a residue which, upon crystallization suitably from acetone/ether yields the substituted carbonyl compound (X) in high yield.

In an alternate mode of the procedure the acid (IX) is treated directly with a lithium organometallic compound. In this procedure the acid (IX) is similarly taken up in an ether, suitably a water-immiscible ether such as tetrahydrofuran. Again, heating may be necessary.

There is prepared, in a similar solvent, a solution of the appropriate organometallic lithium compound. Depending upon the final product desired to be obtained there may be a utilized lithium alkyls such as lithium methyl, lithium ethyl, lithium butyl or the like, there may also be a utilized aryl lithium compounds such as phenyl lithium or naphthyl lithium or aralkyl lithium compounds for example benzyl lithium and the like. The organo lithium compounds are utilized in an exact quantity of 2 moles per mole of acid and are cooled to from between about minus 80° C. to about minus 30° C. suitably to about minus 60° C. The solution of the acid (IX) is added to the solution of the organo lithium compound and the reaction permitted to proceed and the product thereof worked up in a manner similar to that utilized for the organo cuprolithium compound above.

The 6,11-diether (X) is then dealkylated to the corresponding hydroxy compound (XI) by a combination of two reactions. The first involves oxidative demethylation with silver in the presence of nitric acid and the second reduction by an N,N-dialkylhydroxylamine.

The 6,11-diether (X) is then taken up in a water-miscible polar organic solvent suitably a ketonic solvent preferably acetone and there is added thereto a substantial excess suitably from about 2 to about 4 equivalents of silver oxide. The mixture is agitated to disperse the silver oxide and warmed to a temperature of from about 30° C. to about 60° C. The warmed solution is agitated and there is added thereto aqueous nitric acid suitably having a strength of between 2 N and 8 N preferably about 6 N. While it is preferred to carry out the reaction at approximately 60° C. the reaction is operative in a temperature range of between 0° C. and 80° C. After addition of the nitric acid the reaction mixture is, suitably, permitted to stand at ambient temperature for from about 30 minutes to about one hour suitably for about 1 hour and the solvent removed under reduced pressure. The residue is treated with water and a water-immiscible reaction inert organic solvent suitably a halocarbon solvent preferably methylene chloride, the organic phase separated, dried, and the solvent removed to leave a sticky reddish residue which is utilized without further purification. The red residue is taken up in a reaction inert water-immiscible polar organic solvent suitably an alkanolic ester most suitably ethyl acetate and treated with an organic reducing agent suitably a basic reducing agent for example an N,N-dialkylhydroxylamine preferably diethylhydroxylamine. The reaction proceeds at between 0° and 60° C., most suitably at ambient temperature and is complete in between 15 minutes to one hour suitably after 30 minutes. The reaction mixture is then quenched by the addition of dilute aqueous hydrochloric acid the organic layer separated dried, and the solvent removed under reduced pressure to yield, on recrystallization, suitably from methylene chloride ether, the corresponding 6,11-dihydroxy tetrahydronaphthacenequinone (XI) as red needles which, in the daunomycin series, are the known 7,9-dideoxydaunomycinone, a known intermediate for the synthesis of daunomycin.

PREPARATION OF STARTING MATERIALS

Certain of the compounds falling within the scope of formula (II) are new compounds and may be prepared in accordance with the general procedures set forth below.

The benzene 1,4-diether (XX) is converted into the corresponding aldehyde by reaction with a gem-dihalomethyl ether suitably a gem-dichloromethyl ether in the presence of a Lewis acid. There are utilized substantially stoichiometric quantities of all three reagents. Any Lewis acid such as those set forth hereinabove may be utilized. However, stannic chloride is especially preferred. The reaction is carried out in an organic water-immiscible solvent suitably a halogenated hydrocarbon solvent such as methylene chloride or the like. The reaction may be carried out in a temperature range of between minus 10° C. and about plus 25° C. most suitably at about 0° C. The reaction is very rapid and is complete in between 2 and 15 minutes. The reaction mixture is quenched with dilute aqueous acid and the organic phase washed, dried, and the solvent removed under reduced pressure to yield the corresponding aldehyde (XXI).

The aldehyde (XXI) is then condensed with the appropriate malonic ester (XXII). ($R_9=R_{10}=COOR_{15}$). The nature of the ester group is not critical since, as was shown above, it will eventually be removed, however it should be higher than methyl since a selective hydrolysis of a methyl ester is called for in a later step. Any dialkyl malonate may be utilized. Diethylmalonate being convenient from the point of view of availability. Substantially stoichiometric amounts of the aldehyde (XXI) and the malonic ester are taken up in a reaction inert organic solvent capable of forming an azeotropic mixture with water. Catalytic amounts of base, suitably piperidine and carboxylic acid, suitably acetic acid added and the mixture heated under reflux until no further azeotropic distillate is obtained. Typically, the reaction will be complete in from about 6 to about 12 hours. The mixture is then washed with dilute acid, water, and saturated aqueous bicarbonate solution. The solvent is removed to yield the corresponding benzylidene malonate (XXIII) which is then hydrogenated to the corresponding benzylmalonate (XXIV).

It should be noted that in the foregoing procedures compound (XXI) is an aldehyde of a type heretofore difficult to obtain. Well-known Friedel-Crafts procedures exist for the formation of corresponding ketones. Thus where it is desired to produce a final product having, say, an alkyl substituent at C-10, ($R_{13}=$alkyl) that substituent is present on the carbonyl of (XXI) in place of the aldehydic hydrogen.

The reduction is suitably carried out by catalytic hydrogenation suitably in the presence of a palladium-charcoal catalyst.

The benzylidene malonate (XXIII) is taken up in an inert organic solvent suitably a lower alkanol or an alkyl alkanoate preferably ethyl acetate or the like. The catalyst is added to the solution. There is utilized about 2–3% by weight of catalyst relative to the benzylidene malonate. It is preferred to utilize a catalyst carrying approximately 10% of the active catalytic material on the carrier suitably 10% palladium-on-charcoal. Hydrogen absorption is carried out in the usual manner at ambient pressure and temperature and is substantially theoretical and is complete between about 2 to about 3 hours.

The hydrogenation mixture is filtered to remove the catalyst and yields, upon removal of the solvent the desired benzyl malonate (XXIV).

The benzyl malonate (XXIV) is then condensed with a suitable haloalkanoic ester. The nature of the ester group is not critical, however, it should be more labile than that present in the malonate (XXII).

Later in the reaction sequence this ester function, i.e., $R_8$, must be selectively removed in the presence of other ester functions (i.e., $R_{15}$). For convenience $R_8=$methyl, is preferred because it can be selectively saponified. However the trichloroethyl group may also be used since it can easily be selectively removed by zinc in acetic acid. The alkyl moiety chosen will depend upon the size of ring A desired and its substitution pattern. Thus, if it is desired to form, at the end of the synthetic sequence, ring A carrying no substituents at what will become the 8-position of the ring then the haloalkanoate is a haloacetate suitably a bromoacetate. If, for example, it were desired to place, say, a methyl substituent at this position then there would be utilized an alpha bromopropionate.

The benzyl malonate (XXIV) is taken up in a dry inert organic solvent suitably an aromatic hydrocarbon solvent most suitably benzene and added to a suspension of a strong base in a similar solvent. Among these bases sodium hydride is especially preferred. A trace of alkanol, suitably, is added to initiate the reaction and the mixture heated under reflux until evolution of hydrogen ceases. The reaction mixture is then cooled and the appropriate alkyl haloalkanoate in a similar solvent is added. The reaction mixture is heated, suitably under reflux and cooled. The reaction mixture is then quenched by the addition of a small amount of organic acid in the same solvent, suitably acetic acid in benzene and the reaction mixture worked up in the usual manner to yield the desired compound (XXV) in this sequence (which is the same as compound (II) in the principal reaction sequence).

EXPERIMENTAL

EXAMPLE I 2,5-Diethoxybenzaldehyde (XXI)

A mixture of 1,4-diethoxybenzene (24.9 g 0.150 mole) and 1,1-dichloromethyl methyl ether (18 g., 0.157 mole) in methylene chloride (80 ml.) was added with stirring during 20 minutes to a solution of stannic chloride (39 g., 0.150 mole) in methylene chloride (150 ml.) at approximately 0° C. The solution was then stirred at this temperature for 5 minutes and quenched by addition of aqueous hydrochloric acid (6 N., 100 ml.) which was added rapidly. The organic phase was separated washed with saturated aqueous sodium bicarbonate, dried over anhydrous magnesium sulfate, filtered, and the solvent removed from the filtrate by evaporation under reduced pressure to yield a crystalline solid (29 g.) m.p. 57°–59° C. Recrystallation (from ether) gave 2,5-Diethoxybenzaldehyde (27.1 g., 0.138 mole, 93%) m.p. 60°–61° I.R.: 1738 cm$^{-1}$ (aldehyde CO).

In accordance with the above procedure but starting, in place of 1,4-Diethoxybenzene with 1,4-Dimethoxybenzene or 1,4-Dipropoxybenzene or 1,4-Diisopropoxybenzene there is obtained the corresponding 1,4-Dimethoxybenzaldehyde or 1,4-Dipropoxybenzaldehyde or 1,4-Diisopropoxybenzaldehyde respectively.

EXAMPLE II

Diethyl 2,5-Diethoxybenzylidenemalonate 2,5-Diethoxybenzaldehyde (24 g., 0.124 mole) and diethyl malonate (20 g., 0.125 mole) are added to a solution of piperidine (3.0 g.) and glacial acetic acid (6 ml.) in benzene (160 ml.). The mixture is heated under reflux utilizing a Dean-Stark water separater until water ceased to be separated. After 8 hours of distillation 2.3 ml. of water out of a theoretical yield of 2.23 ml. are obtained and the reaction mixture cooled. The cooled reaction mixture is washed with aqueous hydrochloric acid (6 N, 70 ml.) water (70 ml.) and aqueous sodium bicarbonate (5% w/w, 50 ml.). The organic layer is separated, dried over magnesium sulfate, filtered, and the solvent removed under reduced pressure to yield a yellow oil (42.7 g., 0.127 mole, 100%). Trituration with petroleum ether yields diethyl 2,5-Diethoxybenzylidenemalonate (38.4 g., 0.114 mole, 92%) m.p. (from petroleum ether) 52°–53° C. I.R.: 1720 cm$^{-1}$ mass spec m/e 336.

In accordance with the above procedure but where, in place of diethyl malonate, there is employed dimethyl malonate, dipropyl malonate or dibenzyl malonate, there is obtained the corresponding dimethyl, dipropyl, or dibenzyl, 2,5-diethoxybenzylidenemalonate.

Similarly, but starting with 1,4-dimethoxybenzaldehyde or 1,4-dipropoxybenzaldehyde or 1,4-diisopropoxybenzaldehyde in place of 1,4-diethoxybenzyldehyde there is obtained, in accordance with the principal reaction, diethyl 2,5-dimethoxybenzylidenemalonate or diethyl 2,5-dipropoxybenzylidenemalonate or diethyl 2,5-Diisopropoxybenzylidene malonate.

In accordance with the principal example but where, in place of 2,5-diethoxybenzaldehyde there is utilized 2,5-diethoxybenzyl methyl ketone or 2,5-diethoxybenzyl benzyl ketone there is obtained ethyl 2-ethoxycarbonyl-3-(2',5'-diethoxyphenyl) crotonate and ethyl 2-ethoxycarbonyl-3-(2',5'-diethoxyphenyl)-4-phenylcrotonate respectively.

EXAMPLE III

Diethyl(2,5-Diethoxybenzyl)malonate

Diethyl 2,5-diethoxybenzylidine malonate (35.3 g., 0.105 mole) is taken up in ethyl acetate (100 ml.) in the presence of a palladium-on-charcoal catalyst (10%, 0.5 g.). The mixture is hydrogenated, with agitation, at ambient pressure and temperature hydrogen absorption (2545 ml.; theoretical: 2550 ml.) ceases abruptly after 2.5 hours. The mixture is filtered to remove the catalyst and the solvent removed under reduced pressure to yield diethyl 2,5-diethoxybenzyl malonate as a colorless oil (35.6 g., 0.105 mole, 100%) which is not purified further.

I.R. 1738 cm$^{-1}$ nmr (d$_6$-acetone) ppm. 1.0–1.6 (m, 12H);

3.12 (d, 2H L=7 Hz.); 3.68 (t, 1H, L=7 Hz); 3.7–4.3 (m, 8H); 6.67 (s, 3H).

In accordance with the above procedure but starting with any of the 2,5-Dialkoxybenzylidene malonates produced in accordance with Example II there are obtained the corresponding 2,5-dialkoxybenzyl malonates.

EXAMPLE IV

Methyl 4-(2',5'-Diethoxyphenyl)-3,3-bis(ethoxycarbonyl) butyrate

Diethyl 2,5-diethoxybenzyl malonate (24.8 g., 0.073 mole) is taken up in dry benzene (120 ml.) and the resultant solution added to a suspension of sodium hydride (2.66 g., 0.11 mole) in dry benzene (45 ml.). Ethanol (50 µl) is added and the mixture heated under reflux for 4 hours. Hydrogen evolution is noted and ceases after 4 hours. The mixture is then cooled to ambient temperature and a solution of methyl bromoacetate (12.4 g., 0.081 mole) in benzene (25 ml.) is added with stirring over a period of 20 minutes. The resultant mixture is heated briefly under reflux (5 to 15 minutes) then cooled. The reaction is quenched by the addition of a solution of acetic acid in benzene (5 ml./20 ml.) which is added slowly with stirring. The quenched reaction mixture is allowed to stand overnight, then washed with water (200 ml.) and aqueous sodium bicarbonate (5%, 40 ml.), the organic layer separated and dried over magnesium sulfate, filtered, and the solvent removed under reduced pressure to yield methyl 4-(2',5'-diethoxyphenyl)-3,3 -bis(ethoxycarbonyl) butyrate as a pale brown oil (27.8 g., 0.068 mole, 92.5%). nmr shows this product to be essentially pure and it is not further purified in the next step.

I.R. 1738 cm$^{-1}$ (COOR)

nmr (d$_6$-acetone) ppm.

1.22 (t,6H); 1.32 (t,6H); 2.7 (s,2H); 3.3 (s,2H); 3.56 (s,3H); 3.6–4.3 (m,8H); 6.5 (m,3H).

In accordance with the above procedure but, in place of methyl bromoacetate, using methyl chloroacetate, methyl iodoacetate, or β,β,β-trichloroethyl bromoacetate there is obtained in the first three instances the same product as in the principal example and in the last case the corresponding B,B,B-trichloroethyl butyrate respectively.

In accordance with the procedures in the principal example but, in place of methyl bromoacetate, using methyl 2-bromopropionate, or methyl 2-bromoisobutyrate there is obtained the corresponding methyl 4-(2',5'-diethoxyphenyl)-3,3-bis(ethoxycarbonyl)-2-methyl and 2,2-dimethylbutyrate respectively.

In accordance with the principal example but where, in place of 2,5-diethoxybenzaldehyde there is utilized 2,5-diethoxybenzyl methyl ketone or 2,5-diethoxybenzyl benzyl ketone there is obtained ethyl 2-ethoxycarbonyl-3-(2',5'-diethoxyphenyl)-4-phenylcrotonate respectively.

EXAMPLE V

Methyl 3,3-bis(ethoxycarbonyl)-4-[(2',5'-dimethoxy-4'-(4''-methoxy-3''-phthalido)]phenylbutyrate 4-Methoxy-3-bromophthalide (I) (16.5 g., 0.068 mole) is dissolved in methylene chloride (60 ml.) and added to a solution of methyl 3,3-bisethoxycarbonyl-4-(2',5'-diethoxyphenyl) butyrate (II) (27.3 g., 0.067 mole) in methylene chloride (60 ml.). There is separately prepared a solution of stannic chloride (23 g., 0.088 mole) in methylene chloride (80 ml.). The mixed solutions of compounds I and II are added drop-wise to the foregoing solution of stannic chloride initially at room temperature and stirred vigorously for approximately 1 hour. During the course of the reaction the temperature rises to 35° C. After addition is complete the reaction mixture is permitted to stand at ambient temperature for a further 4 hours. Ice-cold aqueous hydrochloric acid (4 N, 100 ml.) is added with stirring, and stirring is continued for a further 15 minutes. The organic layer is separated, washed with water and saturated aqueous sodium bicarbonate solution, dried over magnesium sulfate, filtered, and the solvent removed from the filtrate under reduced pressure to yield a yellow oil (38.1 g.); which upon crystallization from ether yields:

Methyl 3,3-bis(ethoxycarbonyl)-4[(2',5'-dimethoxy-4'-(4''-methoxy-3''-phthalido)]phenylbutyrate (III) (31.4 g., 0.055 mole, 82%) m.p. (from ether) 114°–116° C. I.R.: 1770 cm$^{-1}$ (lactone carbonyl), 1738 cm$^{-1}$ (ester carbonyl).

nmr (d$_6$-acetone) (ppm)

1.23 (t, J=6.5 Hz; 12H); 2.9 (s, 2H); 3.43 (s, 2H); 3.70 (s, 3H); 3.7–4.4 (m, 8H); 6.5 (s, 1H); 6.67 (m, 2H); 7.13 (m, 1H); 7.54 (m, 2H).

Mass spec: m/e 572, (parent) 341 (loss of CH$_3$OCO CH$_2$C(CO$_2$C$_2$H$_5$)$_2$ In accordance with the above procedures but where, in place of 3-bromo-4-methoxyphthalide there is employed the corresponding 3-chloro- or 3-iodo-4-methoxyphthalide there is obtained the same product.

In accordance with the above procedure but, where in place of 3-bromo-4-methoxyphthalide there is employed the corresponding 3-bromophthalide; 3-bromo-4,7-dimethoxyphthalide, 3-bromo-4,7-dimethylphthalide; 3-bromo-5,6-dimethylphthalide; 3,4,7-tribromophthalide, 3,5,7-tribromophthalide, 3,5,6-tribromophthalide, 3-bromo-5,6-dichlorophthalide, 3-bromo-5,7-dimethoxyphthalide, 3-bromo-4,6-dimethoxyphthalide, 3-bromo-5,7-dimethylphthalide, 3-bromo-4,6-dimethylphthalide, 3-bromo-7-halo-4-methoxyphthalide, 3-bromo-4-halo-7-methoxyphthalide, 3-bromo-halo-4-methoxyphthalide, 3-bromo-5-halo-4-methoxyphthalide, 3-bromo-5-halo-7-methoxyphthalide, 3-bromo-6-halo-7-methoxyphthalide, 3-bromo-4-halo-5-methoxyphthalide, 3-bromo-4-halo-6-methoxyphthalide, (where halo is F, Cl, Br or I) there are obtained methyl 3,3-bis(ethoxycarbonyl)-4-[(2',5'-dimethoxy-4'-(3''-phthalido)]-phenylbutyrate and the compounds corresponding to the phthalide substitution patterns described in the foregoing paragraph.

EXAMPLE VI 3,3-Bis (ethoxycarbonyl)-4-[2',5'-dimethoxy-4'-(4''-methoxy-3''-phthalido)]phenylbutyric acid (IV)

Methyl 3,3-bis(ethoxycarbonyl)-4-[2',5'-dimethoxy-4'-(4''-methoxy-3''-phthalido)]phenylbutyrate (III) (25 g., 0.046 mole) is taken up in tetrahydrofuran (200 ml.) and methanol (200 ml.); an aqueous solution of potassium hydroxide (3.35 g., 0.060 mole, 200 ml.) is added thereto. The mixture is heated under reflux for 4 days and the solvent substantially removed thereafter by evaporation under reduced pressure. The residue is acidified with dilute aqueous hydrochloric acid (1 N, 100 ml.) and extracted with methylene chloride (300 ml.) the organic phase is washed with water (100 ml.), dried over anhydrous magnesium sulfate, filtered, and the solvent removed from the filtrate under reduced pressure to yield 3,3-Bis(ethoxycarbonyl)-4-[2',5'-dimethoxy-4'-(4''-methoxy-3''-phthalido)] phenylbutyric acid (IV) m.p. 105°–109° C., I.R. (Nujol), 2600, 2800 (broad for CO$_2$H), 1750 (CO of the lactone), 1730 (CO of the ester), 1698 (CO of the CO$_2$H) cm$^{-1}$.

NMR (CDCl$_3$), 10.2 (S,1H), 7.6 (S,1H), 7.5 (S,1H) (M,1H), 6.32 (S,1H), 4.25 (g,4H,J=7 Hz), 3.75 (S,6H,2—OCH$_3$), 3.5 (S,3H,—OCH$_3$), 3.45 (S,2H), 2.9 (S,2H), 1.25 (t,6H,J=7 Hz).

In accordance with the foregoing procedure but starting, in place of the phenylbutyrate of the principal example above, with any of the other phenylbutyrates prepared in accordance with Example V there are obtained the corresponding phenylbutyric acids (IV).

EXAMPLE VII 2,2-Bis(ethoxycarbonyl)-5,8-dimethoxy-6-(2'-carboxy-6'-methoxy)benzyl-1,2,3,4-tetrahydronaphthalene (Vb)

(a) 3,3-Bis(ethoxycarbonyl)-4-[2',5'-dimethoxy-4'-(4''-methoxy-3''-phthalido)] phenylbutyric acid (25 g., 0.047 mole) as prepared in the preceding example is utilized without any further purification and is dissolved in trifluoracetic acid (25 ml.) to which is added trifluoroacetic anhydride (25 ml.). The reaction mixture is allowed to stand at ambient temperature overnight and the solvents removed therefrom under reduced pressure. The residue is made alkaline by the addition of saturated aqueous sodium bicarbonate (100 ml.) and extracted with methylene chloride (300 ml.) The organic phase is separated, washed with distilled water (100 ml.) dried over magnesium sulfate, filtered, and the solvent removed from the filtrate under reduced pressure to yield a greenish sticky compound which is recrystallized (from methanol) to yield 3,3-Bis(ethoxycarbonyl)-5,8-dimethoxy-7-(4'-methoxy-3'-phthalido)-1-tetralone (Va) (20 g., 0.039 moles 85%) as white rosettes of crystals, m.p. 149°–151° C., I.R. (Nujol), 1770 (CO of lactone), 1720, 1740 (CO of the ester), 1690 (CO) cm$^{-1}$ NMR (CDCl$_3$), $\delta$ 7.6 (S,1H), 7.65 (S,1H), 7.4, 7.1 (m,1H) 6.5 (S,1H), 4.25 (g,4H,J=7 Hz) 3.90 (S,3H,—OCH$_3$), 3.75 (S,3H,—OCH$_3$), 3.65 (S,3H,—OCH$_3$), 3.45 (S,2H), 3.15 (S,2H), 1.20 (t,6H,J=7H$_3$).

(b) The keto lactone (Va) produced above, (3.60 g., 0.007 mole) is taken up in trifluoracetic acid (15 ml.) to which is added triethylsilane (2.5 g., 0.022 mole). The reaction mixture is left to stand at ambient temperature for 2 days with agitation. After 2 days a further aliquot of triethylsilane (2.0 g.) is added and after a further week a similar aliquot of triethylsilane was added. After a total reaction time of 2 weeks the solvent is removed under reduced pressure and the residue recrystallized (from ether/petroleum ether) to yield 3,3-bis(ethoxycarbonyl)-5,8-dimethoxy-6-(2'-carboxy-6'-methoxy)-benzyl-1,2,3,4-tetrahydro naphthalene (Vb). (3.2 g., 0.006 mole, 92%) as needle crystals m.p. 134°–136° C.

In accordance with the above procedure but where the first mixture is heated at 60° C. for 12 hours, the second aliquot of triethylsilane added and heated for a further 12 hours, the reaction is then complete with the same product in the same yield.

I.R. (Nujol), 2400–2800 (broad for CO$_2$H), 1730 (CO of the ester), 1680 (CO of CO$_2$H) cm$^{-1}$ NMR (CDCl$_3$) $\delta$ 7.05, 7.75 (M,3H), 6.15(S,1H), 4.5(S,2H), 4.25(g,4H,J=7 Hz). 3.75(S,3H), 3.7(S,3H), 3.6(S,3H), 3.1(S,2H), 2.6, 2.9(M,2H), 2.1, 2.4(M,2H), 1.25 (t,6H,J=7 Hz).

In accordance with the foregoing procedures but, in place of utilizing the compound (IV) of the principal example, there is used as starting material any of the compounds (IV) produced in accordance with Example VI there are obtained the corresponding 5,8-dimethoxy-6-(2'-carboxy) benzyl-1,2,3,4-tetrahydronaphthalenes (Vb)

EXAMPLE VIII 9,9-Bis(ethoxycarbonyl)-12-hydroxy-4,6,11-trimethoxy-7,8,9,10-tetrahydronaphthacene (VI)

2,2-Bis(ethoxycarbonyl)-5,8-dimethoxy-7-(2'-carboxy-6'-methoxy)benzyl-1,2,3,4-tetrahydronaphthalene (1.40 g., 0.0028 mole) is taken up in trifluoracetic acid (3 ml.) and there is added thereto trifluoracetic anhydride (3 ml.) at ambient temperature. After 30 minutes at ambient temperature the solvents are removed under reduced pressure to yield a reaction mixture containing 9,9-Bis(ethoxycarbonyl)-4,6,11-trimethoxy-7,8,9,10-tetrahydronaphthacene-5,12-quinone (VI) existing as a mixture of the keto and enol forms which is utilized without purification in the next step.

In accordance with the above procedure but utilizing any of the other 5,8-dialkoxy-6-(2'-carboxybenzyl)-1,2,3,4-tetrahydronaphthalenes produced in accordance with Example VI there is obtained a similar product.

EXAMPLE IX 9,9-Bis(ethoxycarbonyl)-4,6,11-trimethoxy-7,8,9,10-tetrahydronaphthacene-5,12-quinone (VII)

The product of the principal reaction of example VII (compound VI) has added thereto ice (3 g) and there is added thereto a chromic acid solution of (4 ml.) from a previously prepared solution comprising chromium trioxide (24 g.), concentrated sulfuric acid 30 g, and water to 100 ml. The chromic acid solution is added dropwise with agitation while holding the mixture at 0° C. Thirty minutes after reaction is complete the reaction mixture is removed from the cooling bath and permitted to warm to ambient temperature at which it remains for 2 hours. The reaction mixture is then diluted with distilled water (20 ml.) and extracted with ethyl acetate (20 ml.). The aqueous phase is further extracted with ethyl acetate (20 ml.) and the organic phases iare combined. To the organic phase is added zinc dust (1 g) and the mixture shaken briefly, the zinc dust is removed by filtration and the organic filtrate washed successively with dilute aqueous hydrochloric acid (3 N. 20 ml.) saturated aqueous sodium bicarbonate (20 ml.) and distilled water (20 ml.) The organic extract is dried over anhydrous magnesium sulfate, filtered, and the solvent removed from the filtrate by evaporation under reduced pressure to yield an orange residue which was taken up in methylene-chloride/ethylacetate (17:3, 20 ml.) and passed through a silica gel column: (20 g). The solvent is removed from the eluate under reduced pressure and the residue recrystallized (from aqueous methanol) to give 9,9-Bis(ethoxycarbonyl)-4,6,11-trimethoxy-7,8,9,10-tetrahydronaphthacene-5,12-quinone (VII) (860 mg., 0.017 moles 62%) as yellow needle crystals m.p. 123°–125° C.

I.R. (Nujol), 1722 (CO of the ester),
1670 (CO of the quinone carbonyl group) cm$^{-1}$
NMR (CDCl$_3$), 7.2, 7.8(M,3H), 4.25(g,4H,J=7 Hz) 4.05(S,3H), 4.0(S,3H), 3.9(S,3H), 3.3(S,2H), 2.9(t,2H,J=6 Hz), 2.3(t,2H,J=6 Hz), 1.3 (t,6H,J=7 Hz)

In accordance with the above procedures but starting, in place of 9,9-Bis(ethoxycarbonyl)-12-hydroxy-4,6,11-trimethoxy-7,8,9,10-tetrahydronaphthacene with any of the other anthrone analogs (VI) produced in accordance with Example (VIII) there are obtained the corresponding 5,12-naphthacenequinones.

EXAMPLE X

9-Carboxy-4,6,11-trimethoxy-7,8,9,10-tetrahydronaphthacene-5,12-quinone (IX)

9,9-Bis(ethoxycarbonyl)-4,6,11-trimethoxy-7,8,9,10-tetrahydronaphthacene-5,12-quinone (2.0 g., 0.0040 mole) are dissolved in previously prepared ethanolic potassium hydroxide (potassium hydroxide: 1.5 g, 0.0267 mole; water 10 ml., ethanol 20 ml.). The mixture is heated under reflux for 3 hours during which time a red coloration is noted. The solvent is then removed under reduced pressure and the residue is acidified with dilute aqueous hydrochloric acid (3 N) and extracted with ethylacetate (40 ml.). The organic extract is washed with water, saturated aqueous sodium bicarbonate solution, dried over magnesium sulfate, filtered, and the solvent evaporated from the filtrate under reduced pressure to yield a yellow solid residue which is utilized directly in the next step (if desired this residue may be recrystallized) from methylene chloride ether to yield yellow needle crystals m.p. 222°–224° C.

The above prepared yellow solid is taken up in glacial acetic acid (30 ml.) to which is added piperidine (1.5 ml.). The reaction mixture is heated under reflux for one hour, the solvent removed under reduced pressure and the residue washed with water and extracted with ethyl acetate. The ethyl acetate extract is washed with saturated aqueous sodium bicarbonate, dried over magnesium sulfate, filtered, and the filtrate evaporated under reduced pressure to yield a residue which is recrystallized from ether to yield: 9-Carboxy-4,6,11-trimethoxy-7,8,9,10-tetrahydronaphthacene-5,12-quinone (IX) (1.35 g., 0.0034 mole, 85%) m.p. 133.5°–135° C.

I.R. (Nujol), 2500–2800 cm$^{-1}$ (broad for $CO_2H$), 1700 cm$^{-1}$ (CO of $CO_2H$), 1670 (CO of quinone) cm$^{-1}$ NMR (d$_6$-acetone), δ 7.6 7.9(M,3H), 4.1(S,3H), 4.0(S,6H, —$OCH_3$), 2.7, 3.1(M,7H), *$CO_2H$ (too broad to be observed around at 9 ppm).

In accordance with the above procedure but starting, in place of the starting material of the principal example with any of the other quinones produced in accordance with Example IX there are produced the corresponding 2-Carboxy-1,2,3,4-tetrahydrotetracene-6,-11-quinones.

EXAMPLE XI 7,9-Dideoxydaunomycinone dimethyl ether (X)

9-Carboxy-4,6,11-trimethoxy-7,8,9,10-tetrahydronaphthacene-5,12-quinone (100 mg; 0.25 m mole) is taken up in methylene chloride (5 ml.) and a trace amount of dimethylformamide added thereto. Thionyl chloride (200 mg., 1.7 m mole) is added to the foregoing solution at ambient temperature and permitted to remain at that temperature overnight. The solvent is then removed under reduced pressure, anhydrous benzene (10 ml.) is added and the solvent again evaporated under reduced pressure to remove traces of thionyl chloride. This procedure is repeated 3 times. The NMR spectrum of the product is consistent with that of the acid chloride of the starting material.

The thus prepared acid chloride is taken up in tetrahydrofuran (10 ml.) and warmed gently until the material is dissolved.

Lithium dimethylcuprate is prepared in accordance with the procedure set forth in *Journal American Chemical Society* 94 5106 (1972) in anhydrous dimethylether and cooled under nitrogen to −78° C. (dry ice/isopropanol) and stirred. The warm tetrahydrofuran solution of the acid chloride is transferred to a syringe and added slowly to the lithium dimethylcuprate solution. After 30 minutes stirring the cooling bath is removed and the reaction permitted to come to ambient temperature at which it is permitted to remain for 2 hours. The reaction then is quenched by the addition of saturated aqueous ammonium chloride solution (15 ml.) followed by extraction with ethyl acetate (20 ml.). The organic extract is washed with saturated aqueous sodium bicarbonate, dried over anhydrous magnesium sulfate, filtered, and the solvent removed from the filtrate to yield an orange colored residue. This residue is recrystallized (from acetone/ether) to give 7,9-dideoxydaunomycinone (X) dimethyl ether (82 mg; 0.19 m mole; 80%) as yellow colored needles m.p. 185°–186° C.

I.R. (Nujol), 1700 cm$^{-1}$ (CO of the acetyl group) 1665 cm$^{-1}$ (CO of the quinone carbonyl groups). NMR (d$_6$-acetone), ppm. 7.6–7.9 (m,3H), 4.1(s,3H), 3.9(s,6H, —$OCH_3$), 2.8–3.1(m,7H), 2.3(s,3H).

7,9-Dideoxydaunomycinone Diethyl ether (X) When 9-carboxy-6,11-diethoxy-4-methoxy-7,8,9,10-tetrahydronaphthacene-5,12-quinone is subjected to the same reaction conditions as in the previous example 7,9-dideoxydaunomycinone diethyl ether (X) is obtained in 80% yield m.p. 150°–151° C.

I.R. (Nujol) 1700 cm$^{-1}$ (CO of acetyl carbonyl group), 1665 cm$^{-1}$ (CO of the quinone carbonyl groups). NMR (CDCl$_3$) 7.0–7.7(m,3H), 4.02(g,4H,J=3.5 Hz) 3.92 (s,3H), 2.5–3.4(m,5H), 2.25(s,3H), 1.46(t,3H,J=3.2 Hz) 1.4 (t,3H,J=3.5 Hz).

In accordance with the above procedure but, in place of starting with 9-carboxy-6,4,11-trimethoxy-7,8,9,10-tetrahydronaphthacene-5,12-quinone there are employed any of the other 5,12-quinones prepared in accordance with Example IX, there is obtained the corresponding 9-(substituted) carbonyl-6,11-dialkoxy-7,8,9,10-tetrahydronaphthacene-5,12-quinones carrying the appropriate preinserted substituents, where desired, at the 1-,2-,3-,4-,9- and 10-positions.

EXAMPLE XII 7,9-Dideoxydaunomycinone (XI)

Method (a) 7,9-Dideoxydaunomycinone dimethyl ether (IX) (60 mg., 0.15 m mole) is taken up in acetone (4 ml.) to which is added silver oxide (100 mg., mole) the mixture is stirred vigorously to disperse the silver oxide and heated briefly on a steam bath. To the warm, vigorously stirred solution is added aqueous nitric acid (6 N., 0.2 ml.) and stirring continued at ambient temperature for 1 hour. The solvent is removed under reduced pressure and there is added to the residue, methylene chloride (10 ml.) and water (10 ml.). The methylene chloride phase is separated, dried over magnesium sulfate, and the solvent removed from the filtrate to yield a sticky reddish residue. The residue is taken up in ethyl acetate (5 ml.) and N,N-diethylhydroxylamine (0.1 ml., 1.6 m mole) added thereto. After 30 minutes the reaction mixture is quenched by the addition of aqueous hydrochloric acid (1 N., 3 ml.) and stirred for 10 minutes. The ethyl acetate layer is removed, dried over anhydrous magnesium sulfate, the filtrate filtered and the solvent removed from the filtrate under reduced pressure to yield a red solid which is crystallized (from methylenechloride/ether) to yield 7,9-dideoxydaunomycinone (XI) as red needles (48 mg; yield 83%) m.p. 243°–245° C. Mixed m.p. with an authentic sample 243°–245° C.

I.R. (Nujol) 1720, 1615, 1590 cm$^{-1}$.

NMR (CDCl$_3$) ppm. 13,78(s,1H), 13.43(s,1H), 8.1–7.2(m,3H), 2.27(s,3H), 2.15(m,1H), 1.55(m,2H). U.V. (CH$_2$Cl$_2$) 471, 495, 531 nm.

In accordance with the foregoing procedure but starting where, in place of 7,9-dideoxydaunomycinone dimethyl ether, there is utilized instead as starting material any of the 9-(substituted) carbonyl-6,11-dialkoxy-7,8,9,10-tetrahydronaphthacene-5,12-quinones produced in accordance with the foregoing example there is obtained the corresponding 9-(substituted) carbonyl-6,11-dihydroxy-7,8,9,10-tetrahydronaphthacene-5,12-quinone (XI). Where the starting materials for this reaction are substituted in the 1,2,3,4,8 or 10-position the final product will carry a similar substitution pattern.

Method (b) 7,9-Dideoxydaunomycinone diethyl ether (211 mg; 0.5 m mole) is dissolved in nitrobenzene (3 ml.). To this solution there is added slowly, a solution of anhydrous aluminum chloride (0.668 g; 10 m moles) in nitrobenzene (3 ml.) the temperature of the mixture being maintained at room temperature. The resulting violet-colored solution is then heated at 50° for 20 minutes, Methylene chloride (5 ml.) is added together with a saturated solution (10 ml.) of oxalic acid. The biphasic solution is stirred vigorously for 10 minutes and the organic phase is separated, dried over magnesium sulfate and the methylene chloride removed under reduced pressure. To remove the nitro-benzene the residual liquid is applied to a column of silica gel (10 g) and the nitrobenzene is then eluted with petroleum ether (50 ml.). Elution with 20% ethyl acetate in methylene chloride then affords the desired 7,9-dideoxydaunomycinone. Recrystallization of the latter from methylene chloride/ether gives the pure compound (149 mg; 0.425 m mole; yield 85%) identical in all physical characteristics with the sample prepared according to Method (a).

We claim:

1. A compound of the formula

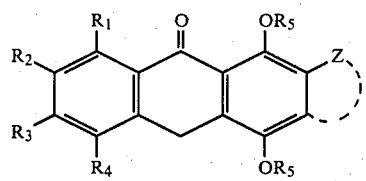

and the enol forms thereof wherein $R_1, R_2, R_3,$ and $R_4$ may also be the same or different and are each selected from the group consisting of hydrogen, alkyl, alkoxy, and halo, $R_5$ is alkyl wherein the alkyl and alkoxy moieties contain 1–5 carbon atoms, Z is $$-CR_{13}H.C(COOR_{15})_2 (CH_2)_2-$$

wherein the bondings indicated at both terminals of the Z group indicate position on the ring of the principal formula, but not stereo chemical orientation, $R_{13}$ is alkyl of 1–5 carbon atoms or hydrogen, $R_{15}$ is lower alkyl of 2–6 carbon atoms.

2. A compound of claim 1 wherein $R_{13}$ is H.

* * * * *